(12) United States Patent
Klug et al.

(10) Patent No.: US 11,580,716 B2
(45) Date of Patent: Feb. 14, 2023

(54) DEVICE FOR A COLOR-BASED DETECTION OF IMAGE CONTENTS COMPUTING DEVICE, AND MOTOR VEHICLE INCLUDING THE DEVICE

(71) Applicant: AUDI AG, Ingolstadt (DE)

(72) Inventors: Markus Klug, Ingolstadt (DE); Tobias Moll, Ingolstadt (DE); Johannes Scheuchenpflug, Baar-Ebenhausen (DE)

(73) Assignee: AUDI AG, Ingolstadt (DE)

( * ) Notice: Subject to any disclaimer, the term of this patent is extended or adjusted under 35 U.S.C. 154(b) by 0 days.

(21) Appl. No.: 17/608,402

(22) PCT Filed: Apr. 30, 2020

(86) PCT No.: PCT/EP2020/062092
§ 371 (c)(1),
(2) Date: Nov. 2, 2021

(87) PCT Pub. No.: WO2020/225112
PCT Pub. Date: Nov. 12, 2020

(65) Prior Publication Data
US 2022/0309759 A1 Sep. 29, 2022

(30) Foreign Application Priority Data
May 3, 2019 (DE) .................... 10 2019 206 363.2

(51) Int. Cl.
| | |
|---|---|
| *G06V 10/143* | (2022.01) |
| *G06V 40/13* | (2022.01) |
| *G06V 10/147* | (2022.01) |
| *B60R 25/25* | (2013.01) |

(52) U.S. Cl.
CPC ............ *G06V 10/143* (2022.01); *B60R 25/25* (2013.01); *G06V 10/147* (2022.01); *G06V 40/1318* (2022.01)

(58) Field of Classification Search
CPC ............... G06V 10/143; G06V 10/147; G06V 40/1318; G06V 40/13; B60R 25/25;
(Continued)

(56) References Cited

U.S. PATENT DOCUMENTS

| | | |
|---|---|---|
| 2015/0277375 A1 | 10/2015 | Large et al. |
| 2018/0232048 A1 | 8/2018 | Popovich et al. |

(Continued)

FOREIGN PATENT DOCUMENTS

| | | |
|---|---|---|
| CN | 107168076 A | 9/2017 |
| DE | 10 2014 011 806 A1 | 2/2016 |

(Continued)

OTHER PUBLICATIONS

English Translation of International Preliminary Report on Patentability and Written Opinion for International Application No. PCT/EP2020/062092 dated Nov. 2, 2021 (5 pages).

(Continued)

*Primary Examiner* — Abhishek Sarma
(74) *Attorney, Agent, or Firm* — Staas & Halsey LLP (57) ABSTRACT

An apparatus for color-dependent detection of image contents includes a light input coupling apparatus, carrier medium, measuring region, output coupling region, and camera apparatus. The light input coupling apparatus includes a light source to emit light at a first wavelength. The carrier medium receives the light and transmits the light by internal reflection to the measuring region. The measuring region includes a first diffraction structure that outputs light at the first wavelength. The first diffraction structure is formed as a multiplex diffraction structure to input light in a second wavelength range. The output coupling region includes a second diffraction structure formed as a multiplex diffraction structure that outputs light at the first wavelength and the second wavelength range. The camera apparatus (Continued)

captures light output from the carrier medium to the camera apparatus, and provides the light in a form of image data which correlates with the light.

17 Claims, 3 Drawing Sheets

(58) Field of Classification Search
CPC ........ B60K 2370/1464; B60K 2370/29; B60K 35/00; B60K 37/06; A61B 5/1079; A61B 5/1171; A61B 5/489; A61B 5/6825; A61B 5/6893; G02B 27/1093; G06F 3/011; G06F 3/0304; G06F 21/32; G07C 9/00563; G03B 33/10
See application file for complete search history.

(56) References Cited

U.S. PATENT DOCUMENTS

2018/0364482 A1\* 12/2018 Georgiou ........... G02B 27/0101
2020/0201051 A1\* 6/2020 Popovich ............ G02B 5/1866

FOREIGN PATENT DOCUMENTS

| DE | 10 2016 206 290 A1 | 10/2017 |
| DE | 10 2016 211 823 A1 | 1/2018 |
| DE | 10 2017 217 193 A1 | 3/2019 |
| DE | 10 2019 206 363.2 | 5/2019 |
| KR | 10-1698102 B1 | 1/2017 |
| WO | 2010/057219 A1 | 5/2010 |
| WO | 2017/060665 A1 | 4/2017 |
| WO | 2018/206450 A1 | 11/2018 |
| WO | PCT/EP2020/062092 | 4/2020 |

OTHER PUBLICATIONS

International Search Report for International Application No. PCT/EP2020/062092 dated Jul. 21, 2020 (15 pages with translation).
Germany Examination Report dated Jan. 24, 2020, for German Application No. 10 2019 206 363.2 (12 pages).
First Examination Report dated Sep. 23, 2022 in related Chinese Patent Application No. 202080032975.6 (8 pages).

\* cited by examiner

DEVICE FOR A COLOR-BASED DETECTION OF IMAGE CONTENTS COMPUTING DEVICE, AND MOTOR VEHICLE INCLUDING THE DEVICE

CROSS REFERENCE TO RELATED APPLICATIONS

This application is a U.S. national stage of International Application No. PCT/EP2020/062092, filed on Apr. 30, 2020. The International Application claims the priority benefit of German Application No. 10 2019 206 363.2 filed on May 3, 2019. Both International Application No. PCT/EP2020/062092 and German Application No. 10 2019 206 363.2 are incorporated by reference herein in their entirety.

BACKGROUND

Described herein is an apparatus for color-dependent detection of image contents, and to a motor vehicle and a computing apparatus having such an apparatus.

There currently are numerous recording systems which facilitate color-dependent recording of image contents by way of light sources at a different wavelengths and by way of color filters. By way of example, this can be used to extend the visible spectrum, for example to recognize surface details, diseases or a biometric identification feature such as a hand vein pattern, for example.

A disadvantage of the previous recording systems is that the light source cannot be overlaid on an optical axis of a camera and this results in oblique illumination which may lead to a displacement of the position of the image contents, corresponding to a displacement of the optical axis. This circumstance can occur with an increasing number of light sources. Optical elements, for example prisms, provide an option for compensating this displacement; however, these require increased installation space.

German Patent Application No. 10 2016 206 290 A1 describes a camera system having at least one camera module and at least one stray light trap, wherein the at least one stray light trap includes a stray light-reducing structure, for example on its inner side, wherein the stray light-reducing structure includes at least one holographic element, for example a volume hologram.

SUMMARY

Described herein is an apparatus for color-dependent detection of image contents.

The apparatus may be achieved according to the examples described herein. Advantageous developments of the disclosure are disclosed in the following description, drawings, and the claims.

Described herein is an apparatus for color-dependent detection of image contents. The apparatus is equipped with a carrier medium formed as a light guide for transferring input-coupled light, and with a light input coupling apparatus, a measuring region and an output coupling region, which are arranged in different portions of the carrier medium. The light input coupling apparatus includes a light source, wherein the light source is constructed to emit light at a first wavelength and wherein the light input coupling apparatus is arranged and constructed to input couple the light at the first wavelength into the carrier medium. The carrier medium is constructed to transmit the input coupled light from the light input coupling apparatus by internal reflection to the measuring region, wherein the measuring region is formed as a holographic element with a first diffraction structure which is designed to output couple input-coupled light at the first wavelength, which is incident on the first diffraction structure, from the carrier medium and input couple light at the first wavelength, which is incident on the first diffraction structure from outside of the carrier medium, into the carrier medium in the direction of the output coupling region.

Here, the first diffraction structure further is formed as a multiplex diffraction structure which is designed to additionally input couple light in a second wavelength range, which is incident on the first diffraction structure from outside of the carrier medium, in the direction of the output coupling region.

The output coupling region is formed as a holographic element with a second diffraction structure which is formed as a multiplex diffraction structure and designed to output couple light at the first wavelength and light in the second wavelength range, which is incident on the second diffraction structure from the direction of the measuring region, from the carrier medium onto a camera apparatus. The camera apparatus is constructed to capture the light which is output coupled onto the camera apparatus and provide the light in the form of image data which correlate with the captured light.

Expressed differently, the apparatus for the color-dependent detection or recording of images is constructed with a carrier medium for guiding input coupled light, a light input coupling apparatus and two regions, specifically a measuring region and an output coupling region, which may be situated in different portions of the carrier medium. That is to say, the regions are arranged at a distance from one another. By way of example, the carrier medium can be manufactured from glass and/or plastics, wherein the light can be transmitted within the carrier medium by internal reflection, that is to say total-internal reflection. Here, the chrominance relates to the two aforementioned light types, i.e., the first wavelength and the second wavelength range that differs therefrom.

The light input coupling apparatus of the apparatus includes a light source which can emit light at a first wavelength, wherein the light source can have a photodiode or laser diode for example. By way of example, the light input coupling apparatus can input couple the light at the first wavelength into the carrier medium via one or more lenses, but it is also possible for the light input coupling apparatus to include a holographic element with a diffraction structure which is designed to input couple the light at the first wavelength from the light source into the carrier medium. By way of example, the light input coupling apparatus can also be arranged at the output coupling region in such a way that the holographic element with the second diffraction structure can input couple the light at the first wavelength into the carrier medium. The light from the light input coupling apparatus which was input coupled in this way can then be transmitted within the carrier medium to the measuring region, wherein the measuring region has a holographic element with a first diffraction structure which can diffract the light at the first wavelength, which was input coupled into the carrier medium, in such a way that it is output coupled from the carrier medium.

The light at the first wavelength which was output coupled from the measuring region can then be used to illuminate an object at the first wavelength, wherein light at the first wavelength reflected by the object can be input coupled back into the measuring region by the first diffraction structure, into the carrier medium in the direction of the output coupling region. Here, in the direction of the output coupling region means a macroscopic direction from the measuring region along the carrier medium to the output coupling region, or a directional vector in the propagation direction of the light by internal reflection. In this case, an optical path can naturally have a zigzag course due to the internal reflection.

A holographic element, also referred to as a holographic optical element (HOE), is an optical element whose operating principle is based on holography and which can be produced by using holographic methods, that is to say holographic exposure. A holographic element can be formed as an optical grating or diffraction grating for example, wherein, as a matter of principle, an optical grating has periodic structures, so-called grating structures, at least in sections, the structures being able to bring about the physical effect of diffractive light guidance, as is known from mirrors, lenses or prisms, for example. If light is, or if light beams are, incident on the optical grating, wherein the incident light beams satisfy the Bragg equation for example, the light beams are diffracted or deflected by the optical grating. The light can thus be guided for example by interference phenomena of the light rays diffracted by the optical grating.

For example, optical gratings can be constructed to be angle-selective or direction-selective and/or wavelength-selective or frequency-selective with respect to the incident light. Thus, only light that is incident on an optical grating from a certain direction, for example in an angular range of approximately 180 degrees, can be deflected. Light incident on the optical grating from another direction is for example not deflected. Additionally or alternatively, it is also possible for only light at one wavelength, for example a narrow wavelength range, to be deflected by the optical grating at a specific diffraction angle. As a result, only, e.g., a portion of the light in a certain wavelength or frequency range might be deflected by the optical grating while, by contrast, the remaining portion of the light can propagate through the grating without being deflected. At least one monochromatic light portion can thus be split off from polychromatic light that is incident on the optical grating.

The first diffraction structure is further formed as a multiplex diffraction structure, that is to say that a holographic optical grating is capable of diffracting polychromatic light, for example the light at the first wavelength and the second wavelength. These are also called multiplexed volume holographic gratings (in short: MVHG) and can be produced, for example, by changing the periodicity of the grating structure of an optical grating or by arranging a plurality of volume holographic gratings one behind the other, which produces the multiplex diffraction structure.

This additionally allows the first diffraction structure to input couple light in a second wavelength range, which is incident on the diffraction structure from outside of the carrier medium, in the direction of the output coupling region. By way of example, light in the second length range can include external light, i.e., ambient light, which may be incident on the object to be recorded. The second wavelength range might also include only certain portions of the spectrum, for example only a red, green, or blue component of the external light. The light at the first wavelength and in the second wavelength range can then be guided within the carrier medium to the output coupling region potentially formed with a second diffraction structure, the latter in turn being formed as a multiplex diffraction structure and being able to output couple the light, which was input coupled into the carrier medium from outside of the carrier medium, onto a camera apparatus.

The camera apparatus which may include, e.g., CMOS or CCD sensors, for example as a sensor array, and is able to capture the light output coupled in this way and able to record the light in the form of image data which correlate with the captured light. To this end, the sensors of the camera apparatus can be sensitive to different wavelengths of the light, for example by way of beam splitters such as prisms or gratings or by way of color filters or color filter arrangements.

The advantage arising from this embodiment is that a light source at a first wavelength can be added in addition to ambient light in a second wavelength range, wherein the light at the first wavelength can be emitted from the measuring region of the apparatus without requiring a displacement of the position of the light source, as a result of which there is no displacement of the optical axis. Moreover, the holographic elements can save space which would otherwise be required for prisms or gratings.

The apparatus also includes embodiments resulting in additional advantages.

An embodiment provides for the carrier medium to have a cuboid embodiment and the light input coupling apparatus to be attached to a narrow side of the carrier medium and the camera apparatus to be attached to a surface side of the carrier medium. Expressed differently, the carrier medium could for example have an edge in the longitudinal direction a, an edge in the width direction b and an edge in the height direction c, wherein the longitudinal direction a is for example greater than b and c. The light input coupling apparatus can be attached to a narrow side or end side of the carrier medium, i.e., to a side or face spanned by b and c. The camera apparatus can be attached to a surface side of the carrier medium, a surface side being a face spanned by a and b. For example, provision can be made for the measuring region and output coupling region to be arranged offset from one another in the longitudinal direction a, wherein for example a direction of the measuring region in which the light is output coupled and the camera apparatus are arranged spaced apart from one another on opposite surfaces.

However, for example it might only be the opposing surface sides, i.e., the end surfaces of the carrier medium, that are plane parallel or have the same radius of curvature, and the light can be input coupled either by way of a surface side or a narrow side. This means that, for example, any geometric shape with plane parallel surface sides, for example a cylindrical shape, may be provided.

The advantage arising from this embodiment is that the light input coupling apparatus and the camera apparatus can be constructed at a distance from one another, allowing installation space to be saved and a flatter structure to be facilitated.

For example, provision may be made for the first wavelength to be located in the infrared wavelength range, for example in a wavelength range from 800 nanometers to 1000 nanometers. This yields the advantage that an object can be illuminated in the infrared wavelength range as a result of additional involvement of the light source at the first wavelength.

For example, provision may be made for the second wavelength range to be located in the visible wavelength range, for example in a wavelength range from 380 nanometers to 780 nanometers. As a result, the apparatus can record ambient light and additionally superpose infrared light thereon, for example.

An embodiment provides for the measuring region and the output coupling region to be incorporated directly into the carrier medium, for example into a surface structure of the carrier medium, or for the carrier medium to be formed as a separate element from the measuring region and the output coupling region. In the first case, the measuring region and the output coupling region can thus be incorporated directly into a surface structure of the carrier medium, for example. Thus, the carrier medium itself can be embodied in the form of a HOE. In the second case, the measuring region, the output coupling region, and the carrier medium can be formed separately. In this case, the measuring region and the output coupling region can form, for example, at least one first element, and the carrier medium can form a second element that abuts the first element. The measuring region and the output coupling region can thus be formed in at least one HOE. By way of example, the measuring region and the output coupling region can be formed in different sections of a holographic film or plate. To fasten the film or plate to the carrier medium, the film or the plate can be adhesively bonded to the carrier medium. Alternatively, the holographic film can also be embodied in the form of an adhesive film and adhere to the surface of the carrier medium directly, that is to say without adhesive, by molecular forces.

A further embodiment provides the first diffraction structure and the second diffraction structure to be formed as a volume holographic grating or as a surface holographic grating. For example, optical gratings can be produced by exposure of a substrate, that is to say for example photolithographically or holographically. In this context, the optical gratings can then also be referred to as holographic or holographic optical gratings. Two types of holographic-optical gratings are known: surface holographic gratings (in short: SHG) and volume holographic gratings (in short: VHG). In the case of surface holographic gratings, the grating structure can be generated by optically deforming a surface structure of the substrate. Due to the modified surface structure, incident light can be deflected, for example reflected. Examples of surface holographic gratings are so-called sawtooth or blazed gratings. In contrast to this, the grating structure in the case of volume holographic gratings can be incorporated into the entire volume or part of the volume of the substrate. Surface holographic gratings and volume holographic gratings are usually frequency selective, but can also be formed selectively as multiplex or multiplexed volume holographic gratings for a plurality of wavelengths.

A further embodiment provides for the provided image data to be a combination of individual images at the respectively captured wavelength. Combining individual images of the respectively captured wavelength may include for example a mathematical operation applied to the respective images together, for example additive superposition, a subtraction, complementing color regions of the image with image information at a respective wavelength, a convolution, and filtering. For example, provision can be made for it to be possible to present a plurality of planes by a transparency effect which might be generated by adapting the alpha channel of the individual images, it being possible to record the planes by way of an increased penetration depth at the first wavelength, for example. The advantage arising from this embodiment is that data of the individual images can be provided clearly within the image data provided.

A further embodiment provides for the light input coupling apparatus to include a further light source which is constructed to emit light at a third wavelength and wherein the light input coupling apparatus is arranged and constructed to input couple light at the third wavelength into the carrier medium. Here, the first diffraction structure is further constructed to output couple light at the third wavelength, which is incident on the first diffraction structure, from the carrier medium and input couple light at the third wavelength, which is incident on the first diffraction structure from outside of the carrier medium, into the carrier medium in the direction of the output coupling region, wherein the first diffraction structure further is formed as a multiplex diffraction structure which is designed to additionally input couple light at the third wavelength, which is incident on the diffraction structure from outside of the carrier medium, in the direction of the output coupling region. The second diffraction structure which is formed as a multiplex diffraction structure is further designed to output couple light at the third wavelength, which is incident on the second diffraction structure from the direction of the measuring region, from the carrier medium onto the camera apparatus. Expressed differently, the light input coupling apparatus can include a further light source which emits light at a third wavelength and can input couple the light into the carrier medium, wherein the first diffraction structure of the measuring region is able to output couple the light at the third wavelength from the carrier medium and input couple the light into the carrier medium again and the second diffraction structure of the output coupling region can output couple the light at the third wavelength such that the camera apparatus can capture the output coupled light. The advantage arising from this embodiment is that a light source at a further wavelength can additionally be involved in order to make a further feature of an illuminated object visible.

For example, provision may be made for the third wavelength to be located in the ultraviolet wavelength range, for example in a wavelength range between 180 nanometers to 380 nanometers. In this case, provision can be made for the carrier medium to be UV transmissive and be able to guide the latter; for example, the carrier medium may predominantly contain fused quartz.

An embodiment provides for the apparatus to further include an identification device which is constructed to receive the image data from the camera apparatus and to check the image data for a specified biometric identification feature and to generate a control signal should a predetermined comparison condition be met. Expressed differently, an identification device can be provided which receives the image data from the camera apparatus and compares these to a specified biometric identification feature, wherein a control signal can be generated in the case of a predetermined comparison condition. By way of example, the identification device can be a processor which can compare image data to one another, for example a specified biometric identification feature which may be stored in a database of the identification device. Then, a control signal can be generated if the predetermined comparison condition which, for example, allows the similarity of the image data to the specified biometric identification feature to be determined is met. By way of example, the specified biometric identification feature may include a surface structure or pigment structure of the skin of a person, for example of a finger, a line structure or biometric structure, for example a vein structure in the skin, below the surface of a hand of a user or the iris of an eye of a user. The predetermined comparison condition may include for example that a pattern identification yields a correspondence of more than 90 percent. This embodiment yields the advantage that the image data can be checked for a specified biometric identification feature and that a control signal for controlling further appliances can be generated in the case of the correspondence.

Also described herein is a motor vehicle having an apparatus according to any one of the example embodiments described herein, wherein the apparatus may be integrated in a windowpane of the motor vehicle and the control signal controls an unlocking mechanism of the motor vehicle. In this case, controlling the unlocking mechanism can for example include opening a lock of a vehicle door of the motor vehicle. This embodiment yields the advantage of the motor vehicle being able to be opened in a keyless fashion. The motor vehicle described herein is for example may be embodied in the form of a motorized vehicle, for example a passenger car or truck, or as a minibus.

An embodiment of the motor vehicle provides for the apparatus to be integrated in a screen and/or an arm rest of the motor vehicle and for the control signal to control a starting apparatus of the motor vehicle. This embodiment yields the advantage of the motor vehicle being able to be started in a keyless fashion by an authorized user.

Described herein is a computing apparatus having an apparatus according to any one of the embodiments described herein, wherein the apparatus is integrated in a screen of the computing apparatus and the control signal enables access to the computing apparatus. The computing apparatus can include a computer, a tablet PC, and a smartphone, for example. This embodiment yields the advantage that the computing apparatus can be unlocked by the specified biometric identification feature of an authorized user.

The disclosure also includes developments of the apparatus according to the apparatus which have features that have already been described in conjunction with the developments of the motor vehicle described herein. For this reason, the corresponding developments of the apparatus described herein will not be described again here.

The disclosure also includes the combinations of the features of the example embodiments described herein.

BRIEF DESCRIPTION OF THE DRAWINGS

These and other aspects and advantages will become more apparent and more readily appreciated from the following description of the example embodiments, taken in conjunction with the accompanying drawings of which.

DETAILED DESCRIPTION

Reference will now be made in detail to example embodiments, the examples of which are illustrated in the accompanying drawings, wherein like reference numerals refer to like elements throughout.

The embodiments discussed below are example embodiments. In the example embodiments, the described components of the embodiments each represent individual features that should be considered independently of one another and also develop the disclosure in each case independently of one another. The disclosure is therefore also intended to include combinations of the features of the embodiments other than those illustrated. Furthermore, the described embodiments may also be supplemented by further features that have already been described.

In the drawings, identical reference signs each denote elements of identical function.

Figure 1:
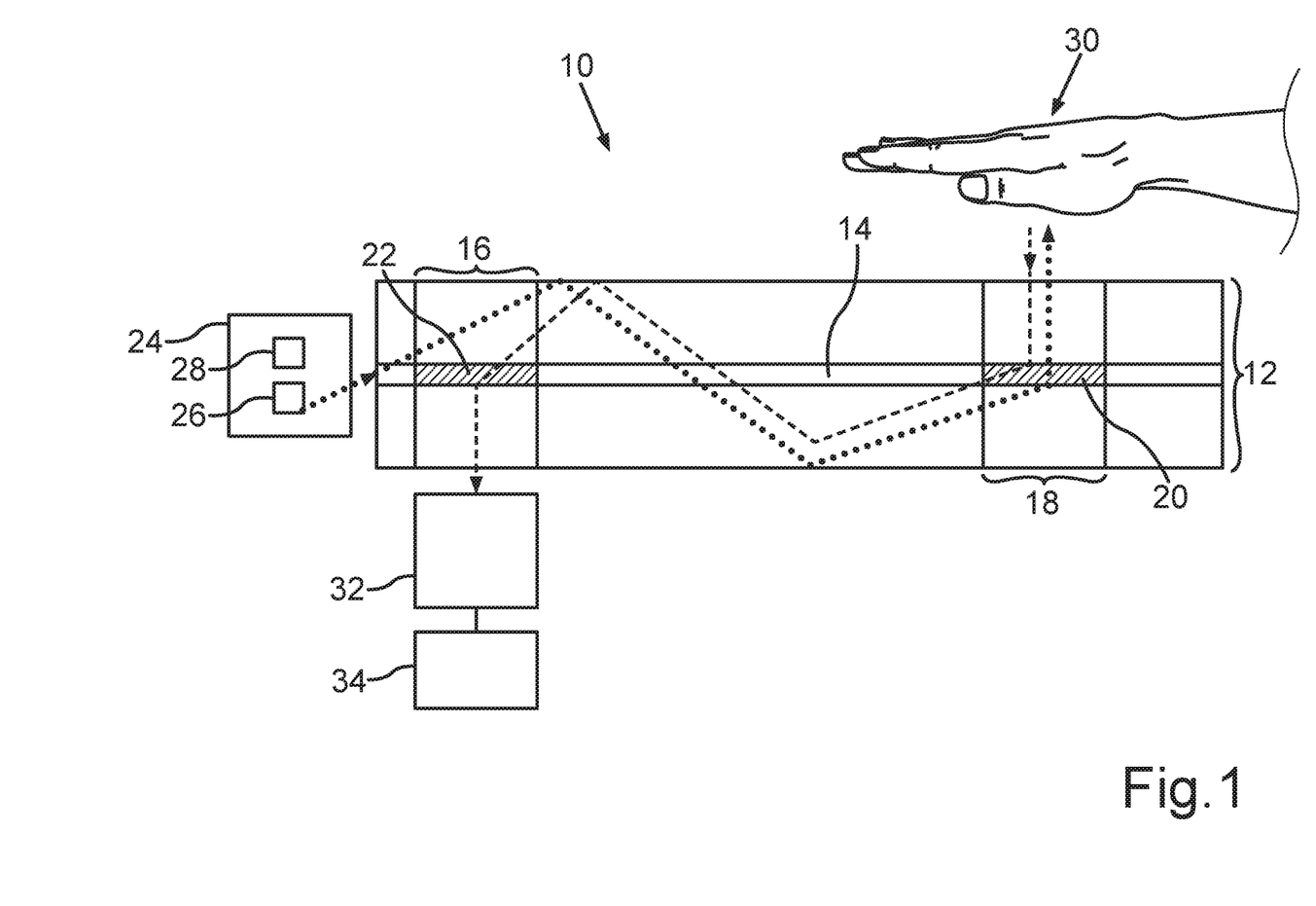
FIG. 1 is a schematic side view of an apparatus according to an example embodiment.

FIG. 1 represents a schematic illustration of an apparatus 10 for color-dependent detection of image contents. The apparatus 10 includes a carrier medium 12 which is formed as a light guide for transmitting input coupled light by way of internal reflection.

The carrier medium 12 can have a cuboid embodiment, for example with separate cuboid elements, i.e., plates, which are constructed to form the carrier medium as a sandwich structure. By way of example, the carrier medium 12 can include two glass plates which serve as light guides and which form the capping layers of the carrier medium. The core of the carrier medium enclosed by the two glass plates may have a holographic element 14 which may be formed as a transparent photopolymer film, for example. With a respective surface, the glass plates directly abut opposite surfaces of the holographic element. Expressed differently, the holographic element 14 and the glass plates abut one another in a planar fashion with their respective faces enclosed by a longitudinal and width side. In addition to guiding light, the glass plates can also protect the holographic element 14 from external environmental influences. For example, FIG. 1 shows a sectional image of the apparatus for color-dependent detection of image contents, in which the apparatus 10 is illustrated with a cut along a longitudinal axis.

The carrier medium 12 can include an output coupling region 16 and a measuring region 18, which are arranged in different portions of the carrier medium and which are arranged offset from one another, for example in a direction of longitudinal extent of the carrier medium. In the output coupling region 16 and in the measuring region 18, the holographic element 14 may have been exposed for the respective region by using holography methods in such a way that a first diffraction structure 20 can form in the measuring region and a second diffraction structure 22 can form in the output coupling region, which diffraction structures can be formed for example as volume holographic gratings or as surface holographic gratings. This means that the first and second diffraction structure 20, 22 have a grating structure that can diffract light at a specified wavelength through a predetermined angle. In this case, the measuring region and the output coupling region can be incorporated directly into the carrier medium or the regions can be formed as a separate element to the carrier medium.

Moreover, the apparatus 10 includes a light input coupling apparatus 24, which may be attached to a narrow side or end side of the carrier medium. The light input coupling apparatus 24 can for example include an infrared light source 26 and a UV light source 28 which can be additionally involved to the benefit of the apparatus 10 depending on the application.

Here, the infrared light source 26 can emit light at a first wavelength which is located in the infrared wavelength range, i.e., for example in a wavelength range from 800 to 1000 nanometers. For example, the infrared light source 26 can have a photodiode which emits light at a wavelength of 850 nanometers. The UV light source 28 can emit light at a third wavelength, wherein the third wavelength is located in the ultraviolet wavelength range, for example between 180 to 380 nanometers. For example, the UV light source 28 can also be formed as a light-emitting diode which emits light at a wavelength of 340 nanometers. The wavelengths specified here for the photodiodes are peak wavelengths which specify a range where the spectrum of the light-emitting diode reaches the greatest intensity. In this case, a person skilled in the art knows that this peak wavelength can deviate by a few nanometers, for example by +/−30 nanometers.

The light input coupling apparatus 24 at the end side of the carrier medium 12 is further constructed to input couple the light from the light sources into the carrier medium 12. To this end, provision can be made of, e.g., a lens system (not shown), which satisfies an input coupling condition or resonance condition for the carrier medium 12 and which is capable of input coupling the light into the carrier medium 12 such that it can be transmitted within the carrier medium by total-internal reflection.

In an example embodiment, the infrared light source 26 emits light at the first wavelength into the carrier medium 12, illustrated by a solid dotted line in FIG. 1. The light at the first wavelength is transmitted within the carrier medium by internal reflection to the measuring region, where it is then incident on and diffracted by the first diffraction structure. As a result, the light at the first wavelength can be output coupled from the carrier medium for the purposes of illuminating an object 30.

In this example embodiment, the object 30 to be measured can be a hand of a user and provision might be made, for example, for a hand vein pattern to be determined. The light in the infrared wavelength range may be suitable to this end since infrared light allows a hand vein pattern recognition to be carried out according to known methods. In this case, the infrared light which is emitted from the carrier medium 12 onto the hand 30 can be reflected and can be incident back in the measuring region on the first diffraction structure 20.

In addition to the infrared light, ambient light which was scattered by the hand 30 can enter the measuring region 18 and can be incident on the first diffraction structure 20; this is indicated by a dashed line. The ambient light may be located in a second wavelength range, wherein the second wavelength range may be located in the visible wavelength range from for example, 380 nanometers to 780 nanometers.

The first diffraction structure 20 can further be formed as a multiplex diffraction structure which can diffract light at a predetermined wavelength through a predetermined angle and consequently can input couple the light back into the carrier medium 12. In this case, the multiplex diffraction structure may include a nested diffraction structure wherein a plurality of optical gratings, for example in the form of volume gratings, are generated in one another by virtue of these, during the generation of the multiplex diffraction structure, the holographic element being exposed multiple times in order to generate a plurality of grating structures, wherein a respective grating structure can diffract the light at a different wavelength through a predetermined angle. As an alternative or in addition thereto, provision can also be made for a plurality of holographic elements to be provided in a layer or sandwich structure, which holographic elements are interconnected by way of a transfer adhesive, wherein each layer is formed for a respective wavelength by way of suitable exposure methods. By way of example, provision can be made of three holographic elements adhesively bonded on top of one another, wherein for example one holographic element is sensitive to the infrared range, one to the ultraviolet range and one to the visible wavelength range.

The light input coupled into the carrier medium 12 can then be guided in the direction of the output coupling region where it strikes the second diffraction structure 22, the latter in turn being able to be formed as a multiplex diffraction structure and being able to be designed to output couple the light from the direction of the measuring region out of the carrier medium onto a camera apparatus 32.

The camera apparatus 32 can for example include a photodetector such as, e.g., a CCD detector or a CMOS detector which for example can be formed as a detector array for recording image data. In this case, the image data can be provided in correlation with the captured light. Here, the camera apparatus 32 can for example be attached to or arranged adjacent to a surface side of the carrier medium.

The image data provided by the camera apparatus 32 can for example have a combination of individual images at the respective captured wavelengths, as a result of which in this example embodiment yields an image of the hand 30, on which a hand vein pattern from the individual images of the infrared wavelength can be overlaid. The image data captured thus can then be received by the identification device 34, which may be a computer processor for example.

The identification device 34 can then check the image data for a specified biometric identification feature and generate a control signal if a predetermined comparison condition is met. In this example embodiment, the specified biometric identification feature may include the hand vein pattern, wherein the identification device 34 for example compares the pattern of the recorded hand veins to a specified pattern, i.e., a pattern stored in the identification device, for example in a memory of the identification device, and in the case of a correspondence of for example more than 90 percent is able to generate a control signal that can be used to control further appliances.

Figure 2:
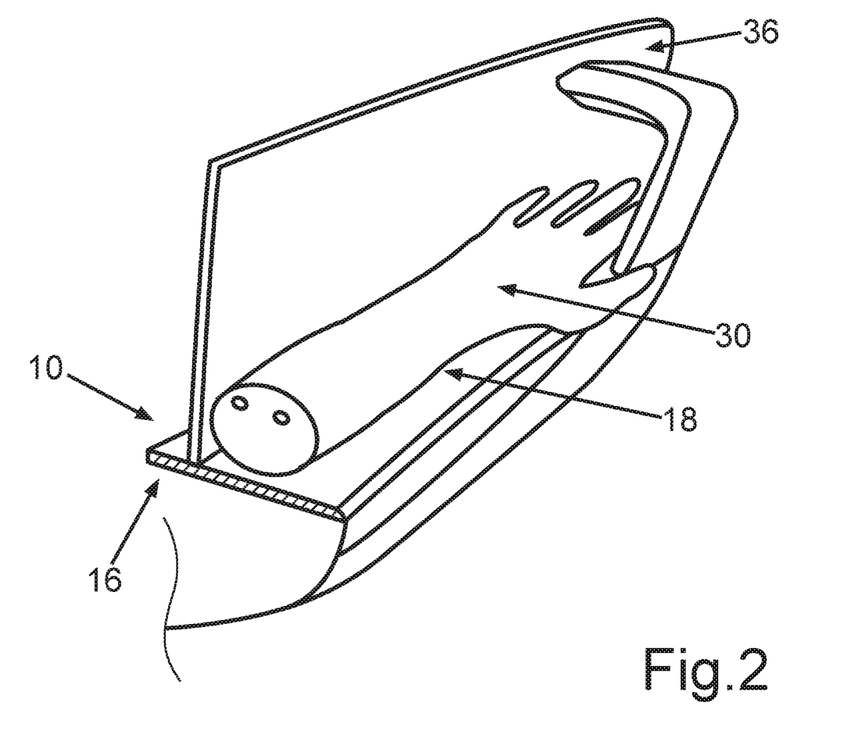
FIG. 2 is an illustration of an inner side of a motor vehicle door according to an example embodiment.

FIG. 2 illustrates an inner side of the motor vehicle 36, for example of a motor vehicle door, according to an example embodiment. The apparatus 10 for color-dependent detection of image contents can be provided in an armrest in the motor vehicle door, for example, in this embodiment. By way of example, to verify their identity, a user can place their hand 30 on the measuring region 18 of the apparatus 10, wherein by way of the above-described method the reflected light can be guided from the hand 30 into the output coupling region 16, which may be housed in the door trim, for example. Additionally, the camera apparatus 32 and the identification device 34 can also be provided in the door trim, wherein the identification device 34, following a check, can, for example, send a control signal to a starting apparatus (not shown) of the motor vehicle, which can start a motor of the motor vehicle.

Figure 3:
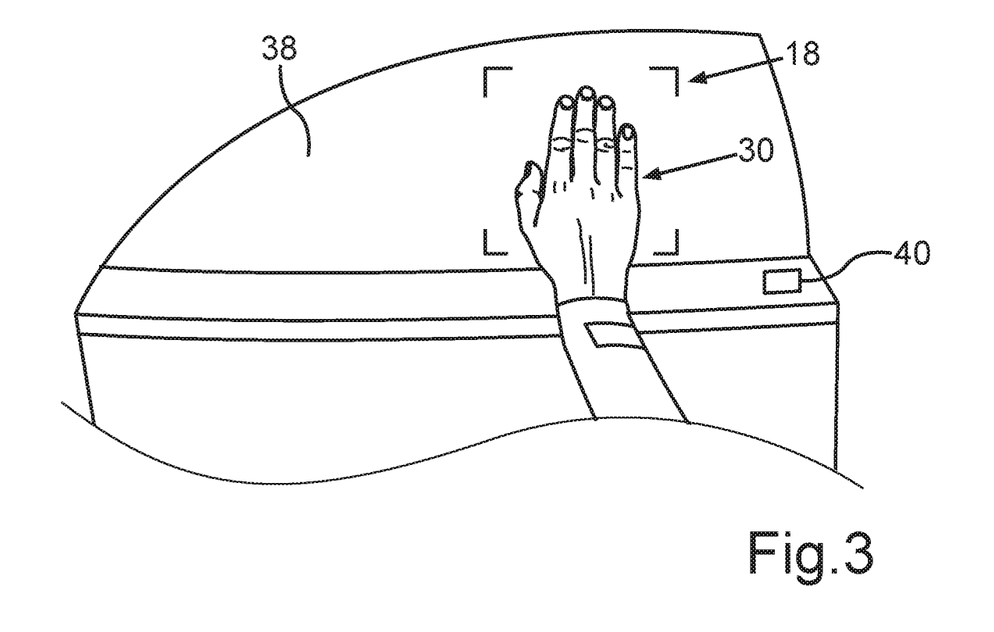
FIG. 3 is an illustration of an outer side of a motor vehicle door according to an example embodiment.

FIG. 3 illustrates a further example embodiment of the apparatus 10. In this example embodiment, the apparatus 10 can be integrated into a windowpane 38 of the motor vehicle. If the hand 30 of the user is placed on the measuring region 18, it is then possible for an image of the hand vein pattern, for example, to be captured and for the latter to be checked by the identification device 34. If the predetermined comparison condition is met, it is possible for example to send a control signal to an unlocking mechanism 40 of the motor vehicle door, which can for example unlock a lock of the vehicle door.

Figure 4:
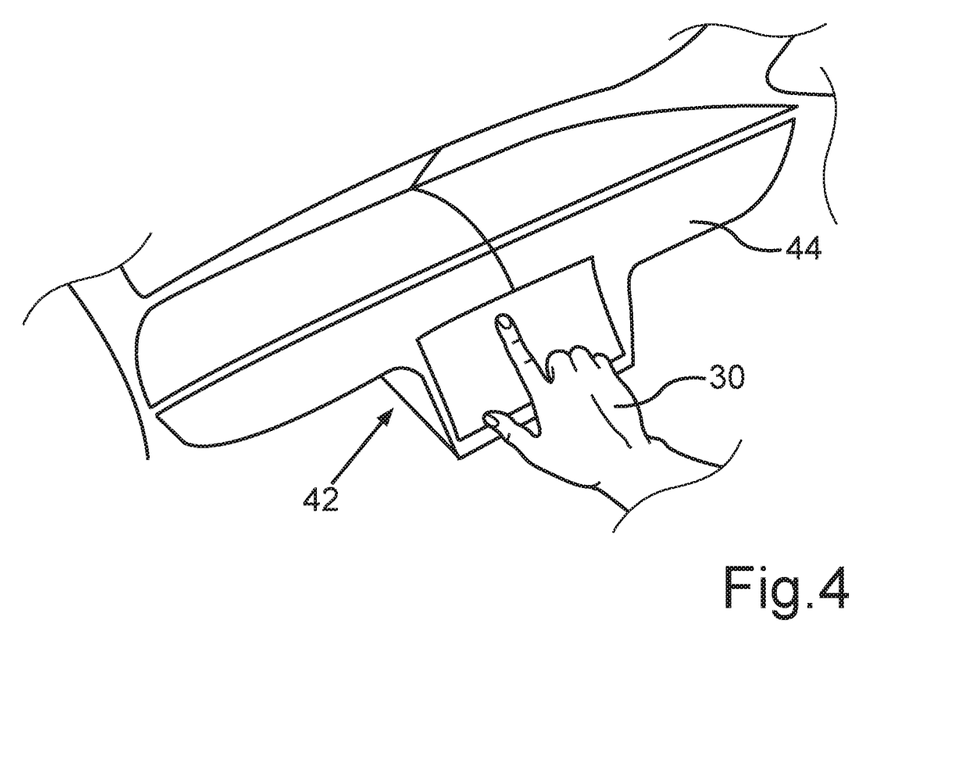
FIG. 4 is an illustration of a computing apparatus in a motor vehicle according to an example embodiment.

FIG. 4 shows an illustration of a computing apparatus 42 according to an example embodiment. In this example embodiment, the computing apparatus 42 is integrated in an instrument panel 44 of a motor vehicle. For example, the computing apparatus 42 can be an infotainment system of the motor vehicle. The computing apparatus 42 can for example have a screen, wherein, in this embodiment, for example, a glass, for example a protection glass, of the screen can be the measuring region 18 of the apparatus 10 for color-dependent detection of image contents. If this is approached by the hand 30, or if the hand makes contact therewith, the above-described hand vein pattern recognition, for example, may take place and access to the computing apparatus 42 may be enabled, for example, in the case of a successful identification.

In an example embodiment, an approach of a hand to the measuring region for hand vein recognition may be sufficient for the recording. This means that the hand need not be placed on the measuring region 18, as a result of which dirtying of the measuring region or dirtying of the hand can be avoided.

Further application options include integrating the apparatus in a gear lever knob, a steering wheel, a rearview mirror, a central console surface, and/or a roof window of the motor vehicle in order to facilitate an identification of a user.

Overall, the examples indicate how the apparatus can provide a color-dependent detection of image contents and a biometric identification by hand vein recognition by way of a holographic element.

A description has been provided with reference to various examples, but it will be understood that variations and modifications can be effected within the spirit and scope of the claims which may include the phrase "at least one of A, B, and C" as an alternative expression that means one or more of A, B, and C may be used, contrary to the holding in *Superguide* v. *DIRECTV*, 358 F3d 870, 69 USPQ2d 1865 (Fed. Cir. 2004). That is the scope of the expression "at least one of A, B, and C" is intended to include all of the following: (1) at least one of A, (2) at least one of B, (3) at least one of C, (4) at least one of A and at least one of B, (5) at least one of A and at least one of C, (6) at least one of B and at least one of C, and (7) at least one of A, at least one of B, and at least one of C. In addition, the term "and/or" includes a plurality of combinations of relevant items or any one item among a plurality of relevant items. That is, the scope of the expression or phrase "A and/or B" includes all of the following: (1) the item "A", (2) the item "B", and (3) the combination of items "A and B".

The invention claimed is:

1. An apparatus for color-dependent detection of image contents, comprising:
   a light input coupling apparatus including a light source configured to emit light at a first wavelength;
   a carrier medium configured as a light guide to receive the light emitted by the light source and to transmit the light emitted by the light source by internal reflection to a measuring region;
   the measuring region disposed on the carrier medium as a holographic element and including a first diffraction structure configured to output light at the first wavelength, which is incident on the first diffraction structure, out of the carrier medium, and to input light at the first wavelength, which is incident on the first diffraction structure from outside of the carrier medium, into the carrier medium in a direction of an output coupling region, wherein the first diffraction structure is formed as a multiplex diffraction structure configured to input light in a second wavelength range, which is incident on the first diffraction structure from outside of the carrier medium, in the direction of the output coupling region;
   the output coupling region disposed on the carrier medium as a holographic element and including a second diffraction structure formed as a multiplex diffraction structure which is configured to output light at the first wavelength and to output light in the second wavelength range, which is from a direction of the measuring region and incident on the second diffraction structure; and
   a camera apparatus configured to capture light which is output from the carrier medium to the camera apparatus via the output coupling region, and to provide the light captured by the camera apparatus in a form of image data which correlates with the light captured by the camera apparatus.

2. The apparatus as claimed in claim 1, wherein
   the carrier medium has a cuboid shape,
   the light input coupling apparatus is attached to a narrow side of the carrier medium, and
   the camera apparatus is attached to a surface side of the carrier medium.

3. The apparatus as claimed in claim 1, wherein the first wavelength is in an infrared wavelength range.

4. The apparatus as claimed in claim 3, wherein the first wavelength is in a wavelength range from 800 nm to 1000 nm.

5. The apparatus as claimed in claim 1, wherein the second wavelength range is in a visible wavelength range.

6. The apparatus as claimed in claim 5, wherein the second wavelength range is in a wavelength range from 380 nm to 780 nm.

7. The apparatus as claimed in claim 1, wherein
   the measuring region and the output coupling region are integrated directly into the carrier medium, or
   the carrier medium is formed as a separate element from the measuring region and the output coupling region.

8. The apparatus as claimed in claim 7, wherein
   when the measuring region and the output coupling region are integrated directly into the carrier medium, the measuring region and the output coupling region are integrated directly into a surface structure of the carrier medium.

9. The apparatus as claimed in claim 1, wherein the first diffraction structure and the second diffraction structure are formed as a volume holographic grating or as a surface holographic grating.

10. The apparatus as claimed in claim 1, wherein the image data includes a combination of individual images which correspond to respective wavelengths.

11. The apparatus as claimed in claim 1, wherein
    the light input coupling apparatus includes a further light source configured to emit light at a third wavelength, and
    the carrier medium is configured to receive the light emitted by the further light source and to transmit the light emitted by the further light source by internal reflection to the measuring region,
    the first diffraction structure is further configured to output light at the third wavelength, which is incident on the first diffraction structure, out of the carrier medium and to input light at the third wavelength, which is incident on the first diffraction structure from outside of the carrier medium, into the carrier medium in the direction of the output coupling region, wherein the first diffraction structure having the multiplex diffraction structure is configured to input light at the third wavelength, which is incident on the first diffraction structure from outside of the carrier medium, in the direction of the output coupling region, and
    the second diffraction structure having the multiplex diffraction structure is configured to output light at the third wavelength, which is from the direction of the measuring region and incident on the second diffraction structure, out of the carrier medium to the camera apparatus.

12. The apparatus as claimed in claim 11, wherein the third wavelength is in an ultraviolet wavelength range.

13. The apparatus as claimed in claim 12, wherein the third wavelength is in a wavelength range between 180 nm to 380 nm.

14. The apparatus as claimed in claim 1, further comprising:
an identification device configured to:
receive the image data from the camera apparatus,
check the image data for a specified biometric identification feature, and
generate a control signal when a predetermined comparison condition is met.

15. A motor vehicle, comprising:
a windowpane;
a display screen;
an arm rest;
an unlocking mechanism;
a starting apparatus; and
an apparatus integrated in at least one of the windowpane, the display screen, and the arm rest, the apparatus including:
a light input coupling apparatus including a light source configured to emit light at a first wavelength,
a carrier medium configured as a light guide to receive the light emitted by the light source and to transmit the light emitted by the light source by internal reflection to a measuring region,
the measuring region disposed on the carrier medium as a holographic element and including a first diffraction structure configured to output light at the first wavelength, which is incident on the first diffraction structure, out of the carrier medium, and to input light at the first wavelength, which is incident on the first diffraction structure from outside of the carrier medium, into the carrier medium in a direction of an output coupling region, wherein the first diffraction structure is formed as a multiplex diffraction structure configured to input light in a second wavelength range, which is incident on the first diffraction structure from outside of the carrier medium, in the direction of the output coupling region,
the output coupling region disposed on the carrier medium as a holographic element and including a second diffraction structure formed as a multiplex diffraction structure which is configured to output light at the first wavelength and to output light in the second wavelength range, which is from a direction of the measuring region and incident on the second diffraction structure,
a camera apparatus configured to capture light which is output from the carrier medium to the camera apparatus via the output coupling region, and to provide the light captured by the camera apparatus in a form of image data which correlates with the light captured by the camera apparatus, and
an identification device configured to receive the image data from the camera apparatus, check the image data for a specified biometric identification feature, and generate a control signal when a predetermined comparison condition is met to control at least one of the unlocking mechanism and the starting apparatus.

16. The motor vehicle as claimed in claim 15, wherein
the identification device includes a memory to store the specified biometric identification feature,
the identification device is configured to compare the image data with the specified biometric identification feature stored in the memory, to determine whether a pattern identification between the image data and the specified biometric identification feature is more than a preset threshold, and
the specified biometric identification feature includes at least one of a surface structure of a skin of a person, a pigment structure of the skin of the person, and a vein structure of the skin of the person.

17. A computing apparatus, comprising:
a display screen; and
an apparatus integrated in the display screen, the apparatus including:
a light input coupling apparatus including a light source configured to emit light at a first wavelength,
a carrier medium configured as a light guide to receive the light emitted by the light source and to transmit the light emitted by the light source by internal reflection to a measuring region,
the measuring region disposed on the carrier medium as a holographic element and including a first diffraction structure configured to output light at the first wavelength, which is incident on the first diffraction structure, out of the carrier medium, and to input light at the first wavelength, which is incident on the first diffraction structure from outside of the carrier medium, into the carrier medium in a direction of an output coupling region, wherein the first diffraction structure is formed as a multiplex diffraction structure configured to input light in a second wavelength range, which is incident on the first diffraction structure from outside of the carrier medium, in the direction of the output coupling region,
the output coupling region disposed on the carrier medium as a holographic element and including a second diffraction structure formed as a multiplex diffraction structure which is configured to output light at the first wavelength and to output light in the second wavelength range, which is from a direction of the measuring region and incident on the second diffraction structure,
a camera apparatus configured to capture light which is output from the carrier medium to the camera apparatus via the output coupling region, and to provide the light captured by the camera apparatus in a form of image data which correlates with the light captured by the camera apparatus, and
an identification device configured to receive the image data from the camera apparatus, check the image data for a specified biometric identification feature, and generate a control signal when a predetermined comparison condition is met to enable access to the display screen.

* * * * *

UNITED STATES PATENT AND TRADEMARK OFFICE
CERTIFICATE OF CORRECTION

PATENT NO. : 11,580,716 B2
APPLICATION NO. : 17/608402
DATED : February 14, 2023
INVENTOR(S) : Markus Klug et al.

It is certified that error appears in the above-identified patent and that said Letters Patent is hereby corrected as shown below:

On the Title Page

Item (54), Column 1, Line 2, delete "CONTENTS" and insert --CONTENTS,--.

In the Specification

Column 1, Line 2, delete "CONTENTS" and insert --CONTENTS,--.

Signed and Sealed this
Fourth Day of April, 2023

Katherine Kelly Vidal
*Director of the United States Patent and Trademark Office*